US010512735B2

(12) United States Patent
Norman et al.

(10) Patent No.: US 10,512,735 B2
(45) Date of Patent: Dec. 24, 2019

(54) FLUID WARMING DEVICE

(71) Applicants: Scott Norman, Stilwell, KS (US);
Mark Petheram, Overland Park, KS (US); Anthony Hash, Olathe, KS (US)

(72) Inventors: Scott Norman, Stilwell, KS (US);
Mark Petheram, Overland Park, KS (US); Anthony Hash, Olathe, KS (US)

(73) Assignee: Neonatal Product Group, Inc., Stilwell, KS (US)

( * ) Notice: Subject to any disclaimer, the term of this patent is extended or adjusted under 35 U.S.C. 154(b) by 510 days.

(21) Appl. No.: 15/282,612

(22) Filed: Sep. 30, 2016

(65) Prior Publication Data

US 2018/0093048 A1    Apr. 5, 2018

(51) Int. Cl.
*A61M 5/44* (2006.01)

(52) U.S. Cl.
CPC ..... *A61M 5/445* (2013.01); *A61M 2205/3368* (2013.01); *A61M 2205/3633* (2013.01); *A61M 2205/3653* (2013.01); *A61M 2205/502* (2013.01)

(58) Field of Classification Search
CPC .. A61M 2205/3368; A61M 2205/3633; A61M 2205/3653; A61M 2205/502; A61M 5/445; A61M 2205/33; A61M 2205/3372; A61M 2205/36; A61M 2205/3646; A61M 2205/366; A61M 2205/3666; A61M 2205/3673; A61M 5/44; F24H 1/0018; F24H 1/121; F24H 1/142; F24H 1/162; F24H 4/02; F24H 2240/00; H05B 1/0244; H05B 1/025; H05B 1/0297

USPC ............................................. 604/114
See application file for complete search history.

(56) References Cited

U.S. PATENT DOCUMENTS

| 5,108,372 | A | 4/1992 | Swenson |
| 6,641,556 | B1 | 11/2003 | Shigezawa |
| 2006/0276864 | A1* | 12/2006 | Collins ............... A61F 7/12 607/105 |

(Continued)

FOREIGN PATENT DOCUMENTS

| JP | 08206205 A | 8/1996 |
| JP | 3090225 B2 | 9/2000 |

(Continued)

OTHER PUBLICATIONS

International Search Report and Written Opinion dated Jan. 11, 2018; for International Patent No. PCT/US2017/053001; International filing date Sep. 22, 2017.

*Primary Examiner* — Jason E Flick
(74) *Attorney, Agent, or Firm* — Hovey Williams LLP

(57) ABSTRACT

A fluid warming device for warming fluids and delivering the fluids to a patient comprises an electrical heating component, a temperature sensor, and a control unit. The electrical heating component warms fluid passing through a fluid-carrying tube and may be positioned along the fluid-carrying tube at a desired location or embedded in the fluid-carrying tube while the control unit is positioned such that the display and user inputs are accessible to a caregiver. The control unit activates the electrical heating component until the fluid-carrying tube is warmed to a desired temperature within a Thermal Neutral Zone (TNZ) as sensed by the temperature sensor.

5 Claims, 9 Drawing Sheets

(56) References Cited

U.S. PATENT DOCUMENTS

| | | | | |
|---|---|---|---|---|
| 2008/0255538 | A1* | 10/2008 | Ellis | A61M 5/44 604/507 |
| 2009/0319011 | A1* | 12/2009 | Rosiello | A61M 5/44 607/105 |
| 2010/0193492 | A1 | 8/2010 | Hughes | |
| 2012/0220938 | A1* | 8/2012 | Saunders | A61F 7/0085 604/114 |
| 2014/0050463 | A1* | 2/2014 | Theilacker-Beck | H05B 1/025 392/466 |

FOREIGN PATENT DOCUMENTS

| | | | |
|---|---|---|---|
| JP | 2007503854 | A | 3/2007 |
| JP | 3963610 | B2 | 8/2007 |
| KR | 1020060019623 | A | 3/2006 |
| WO | WO0162194 | A1 | 8/2001 |

\* cited by examiner

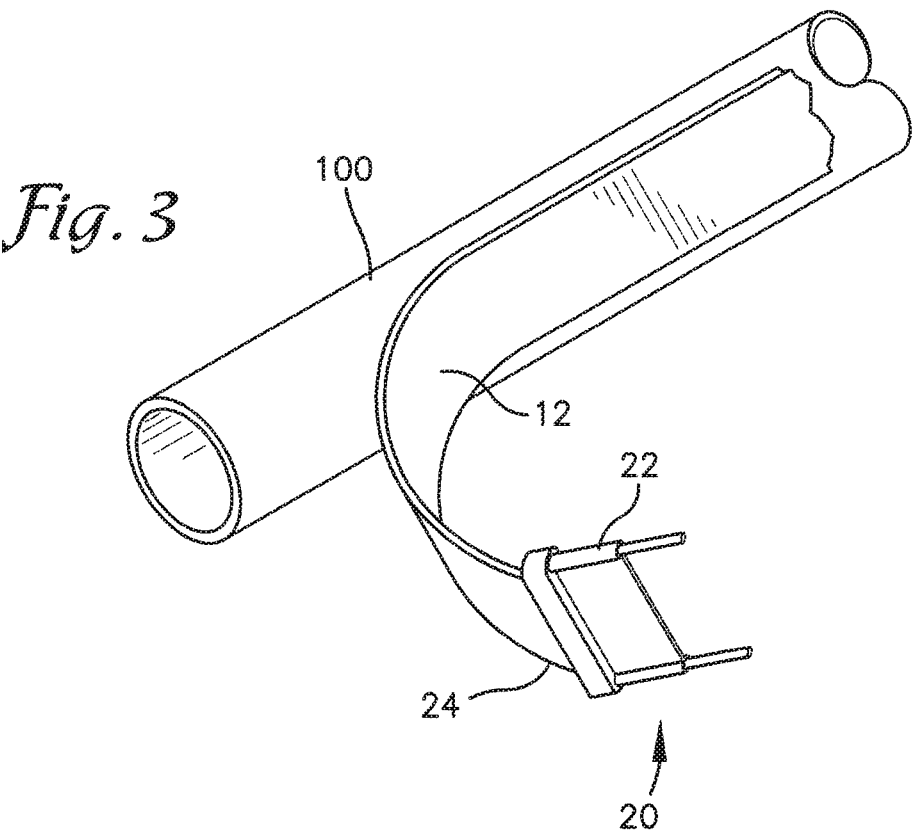
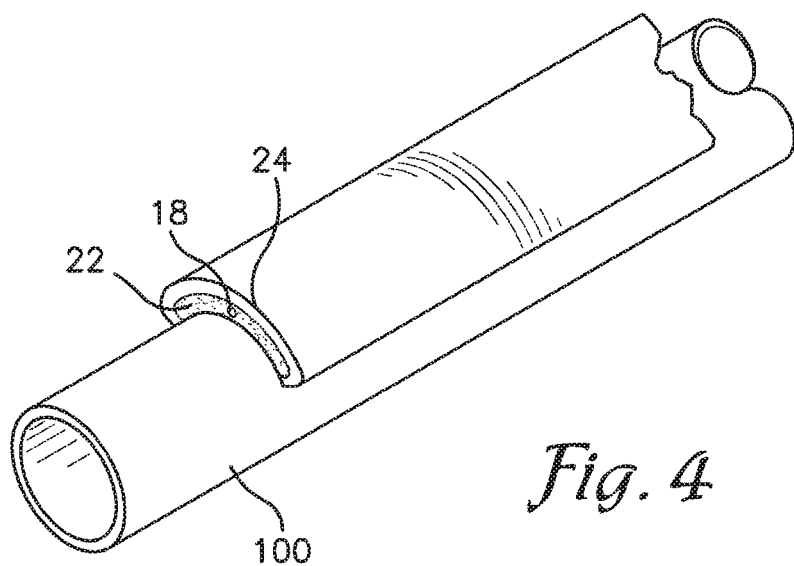

FLUID WARMING DEVICE

BACKGROUND

The present invention relates to fluid warming devices for warming intravenous fluids, enteral feeding fluids and other fluids and delivering them to infants, elderly persons, and other patients (collectively referred to herein as "patients").

Fluid warming devices have been developed to warm fluids as they are being delivered to a patient via a fluid-carrying tube. These devices typically include a housing and a heating element. The housing encloses the heating element and an intermediate portion of a fluid-carrying tube. The fluid-carrying tube is then connected to a pump (or can be gravity fed) at its first end and connected to a patient's vein or stomach at its second end. The fluids are warmed by the heating device as they are pumped or otherwise fed through the fluid-carrying tube.

The heating elements of fluid warming devices are often heated to a temperature of between 120° F. (49° C.) to 140° F. (60° C.). This high temperature level may negatively break down nutrients and medication properties in the fluids. The high heat may also damage the fluid-carrying tubes and introduce foreign particles from the tubes into the fluids.

Another problem with known fluid warming devices is that they transfer a large amount of heat to tubes over a short amount of time due to the limited effective heating length of the warming devices. Some fluid warming devices include elongated channels in their housings for increasing their effective heating lengths and heating times. However, the lengths of the channels are limited by the size of the housings. The housings also must be positioned a long way from patients such that their user inputs and displays are accessible to a caregiver, which often results in the fluids cooling down after exiting the warming devices and before reaching the patients.

SUMMARY

The present invention solves the above-described problems and provides a distinct advance in the art of fluid warming devices. More particularly, the invention provides a fluid warming device that gradually warms fluids to a desired temperature and consistently maintains the desired temperature for delivering the fluids to a patient.

Applicant has discovered that many patients, and infants in particular, experience tolerance issues unless fluids are warmed to a temperature within a Thermal Neutral Zone (TNZ) between 90° F. (32° C.) and 100° F. (38° C.). Temperatures within this range are ideal for fluid adsorption and digestion.

An embodiment of the present invention is a fluid warming device broadly comprising an electrical heating component, a temperature sensor, and a control unit for controlling and powering the electrical heating component in response to temperatures sensed by the temperature sensor. The fluid warming device is especially configured for use with a fluid-carrying tube such as an intravenous tube, an enteral feeding tube, or a syringe.

The electrical heating component warms fluid passing through the fluid-carrying tube and broadly comprises an elongated heating element and a connector. The heating element produces resistive heat when subjected to an electrical current and may be a metal wire, filament, flexible ceramic strip, etched foil heater, or any other element that generates heat. Some embodiments of the heating element may include a heat conductive layer such as teflon, kapton, silicone, or felt and an overlying insulating layer for protecting the heating element and guiding heat from the heating element to the fluid-carrying tube. The connector is electrically coupled with the heating element and configured to plug into the control unit. The connector may be a USB connector, mini USB connector, 4-pin or 16-pin connector, or the like. Alternatively, the heating component may be wirelessly coupled with the control unit.

The temperature sensor senses a temperature of the fluid-carrying tube, the fluid, or the heating element and may be a thermistor, a thermocouple, a silicon bandgap temperature sensor, or any other temperature gauge. The temperature sensor may be positioned near or integrated with the heating element for obtaining a more accurate temperature reading. Alternatively, the temperature sensor may be integrated with the control unit such that the temperature is obtained as a function of a voltage drop across the heating element, a current draw across the heating element, or any other suitable electronic property. The temperature sensor may be coupled with the control unit via the connector described above, a separate connector, or a wireless connection such as via radio frequency (RF).

An embodiment of the control unit includes a controller, a port, a display, a number of user inputs, and a power source, all of which may be contained within or on a housing. The controller regulates a heating level of the heating element in response to temperatures sensed by the temperature sensor and controls the display. The controller may include a printed circuit board (PCB), a memory, and/or other electronic components and is connected to the heating element and the temperature sensor via the port or a wireless connection.

The port provides power to the heating element and receives data from the temperature sensor. The port may have pins for interfacing with a USB connector, mini USB connector, or the like. Two or more ports may be used for separately connecting the heating element connector, a temperature connector, and/or other connectors to the control unit.

The display provides a visual indication of the temperature of the fluid-carrying tube and other information and may be a seven segment LCD display, an analog display, a touch screen, or any other display. The display may include additional LED lights and other indicators for providing additional information to the user. The user inputs allow a user to turn the warming device on and off, to program the warming device, to reset the warming device, and to perform other functions and may include switches, buttons, dials, and other user inputs. The user inputs may comprise a power button or power switch, a reset button, a calibration button, a temperature unit toggle button, and other inputs. The power source supplies electrical power to the heating element, temperature sensor, the controller, and the display and includes a power cord for connecting to a 100 volt or 240 volt, 60 W/hr or 100 W/hr, 50/60 Hz outlet, or any other power outlet. The housing comprises an outer wall forming an internal chamber for enclosing and protecting the controller. The outer wall may also include a port opening for providing access to the port.

In use, the fluid warming device heats fluids to a temperature within the TNZ and delivers the warmed fluids to a patient. To prepare the warming device, a user connects a first end of the fluid-carrying tube to a fluid source via a pump's output. The fluid may also be gravity fed. The user then positions the electrical heating component on or near the fluid-carrying tube. For example, the electrical heating component may be attached to the fluid-carrying tube via an adhesive or wrapped around the fluid-carrying tube. The heating component may also be embedded in the tube. The user then turns on the warming device so that the heating element begins to warm the fluid-carrying tube to a temperature between approximately 90° F. (32° C.) and 103° F. (39° C.). The display indicates the temperature of the fluid-carrying tube and indicates when the warming device is ready for heating the fluid.

Once the warming device is ready to heat the fluid, the user inserts the second end of the fluid-carrying tube into a patient's vein, stomach or intestine. The user then activates or turns on the pump, which directs fluid from the fluid source through the fluid-carrying tube. The fluid may also be gravity fed. The heating element then warms the fluid to a temperature within the TNZ as the fluid passes through the fluid-carrying tube. The warmed fluid then continues through the fluid-carrying tube and into the patient's vein, stomach, or intestine.

The controller maintains the temperature of the fluid-carrying tube between approximately 90° F. (32° C.) and 103° F. (39° C.) when the warming device is on. When the controller determines via the temperature sensor that the fluid-carrying tube is above 103° F. (39° C.) or is above another predetermined temperature, the controller temporarily deactivates the heating element until the temperature has dropped to another predetermined temperature between 90° F. (32° C.) and 103° F. (39° C.).

Importantly, the electrical heating component is configured to be connected to the control unit via the port or a wireless connection, which allows the electrical heating component to be embedded in, attached to, or positioned near the fluid-carrying tube without the control unit being positioned near the fluid-carrying tube. The electrical heating component increases heat transfer to the fluid-carrying tube and may be attached to the fluid-carrying tube lengthwise or in a helical configuration. Alternatively, the electrical heating component (and/or the temperature sensor) are configured to be wirelessly coupled to the control unit.

A fluid warming device constructed in accordance with another embodiment of the invention broadly comprises a heating strip and a control unit. The heating strip combines heating and temperature sensing functions and broadly comprises a heating element, one or more temperature sensors, an overheat sensor, and a connector. The heating strip may be a flat tape or flat ribbon, a round cable, or any other suitable elongated strip. The heating strip may be attached to or positioned near a fluid-carrying tube or any other similar fluid delivery component.

The heating element warms fluid passing through the fluid-carrying tube and may be a metal wire, etched foil heater, filament, ceramic strip, or the like extending from a first end of the heating strip to a second end of the heating strip and back towards the first end so as to form a loop. The heating element may also extend laterally back and forth along the heating strip to increase an overall heat output along the fluid-carrying tube. The heating element produces resistive heat when subjected to an electrical current and may also include a heat conductive layer and an insulating sheath for protecting the heating element and guiding heat from the heating element to the fluid-carrying tube.

The temperature sensors sense a temperature of the fluid-carrying tube, the fluid, or the heating element and may be thermistors, thermocouples, silicon bandgap temperature sensors, or any other temperature gauges. One temperature sensor may be positioned near a proximal end of the heating element while a second temperature sensor may be positioned near a distal end of the heating element for obtaining more complete temperature readings.

The overheat sensor senses an overheating condition and turns off or turns down the heating element for preventing the heating element from warming the fluid-carrying tube to a temperature above an upper limit of the TNZ or another predetermined temperature. The overheat sensor also prevents the heating element from damaging the insulation layer.

The overheat sensor may comprise a single sensor that shuts off or turns down the heating element once the tube reaches a particular temperature or it may comprise several sensors that form a redundant multi-stage sensor assembly that shuts off or turns down the heating element at several successive temperatures. The multi-stage sensor assembly provides redundant temperature protection in case any of the sensors fail.

The connector communicatively connects the heating element, temperature sensors, and overheat sensor to the control unit. The connector may be a USB connector, mini USB connector, 4-pin or 16-pin connector, or any other suitable data connector.

The control unit includes a controller, a port, a display, a number of user inputs, and a power source. The control unit is substantially similar to the control unit described above and is therefore not described in detail here. The control unit may also include a housing configured to retain the controller, port, display, user inputs, and/or power source.

In operation, the heating strip may be attached to or positioned near the fluid-carrying tube such that the temperature sensors and overheat sensor are positioned along the fluid-carrying tube. For example, the heating strip may be attached longitudinally to the fluid-carrying tube or wrapped in a helical configuration around the fluid-carrying tube. The fluid warming device may then warm the fluid-carrying tube as described above. The temperature sensors each may generate a signal representative of a temperature of the fluid-carrying tube. Each temperature sensor may provide different temperature readings since the temperature sensors are spaced from each other along the fluid-carrying tube. The downstream temperature sensor will provide a higher temperature reading than the upstream temperature sensor. The controller may use this difference to determine a rate of temperature increase, a heat transfer efficiency, or other information.

At any time, the overheat sensor may generate a signal representative of an overheating condition. The overheating condition may be a temperature near or at an upper level of the TNZ or another predetermined maximum allowed fluid temperature. The overheating condition may also be a maximum allowed temperature of the temperature sensors or insulating layer. The controller will then turn off or decrease a heat level of the heating element. The controller may also instruct the display to indicate that an overheating condition has occurred or that the fluid warming device needs to be serviced. The controller may then turn on or increase the heat level of the heating element if the overheat sensor no longer senses an overheat condition.

Importantly, the heating strip is configured to be connected to the control unit via the port or a wireless connection, which allows the heating strip to be attached to or positioned near the fluid-carrying tube without the control unit being positioned near the fluid-carrying tube. The heating strip may also be elongated for increasing heat transfer to the fluid-carrying tube and may be attached to the fluid-carrying tube longitudinally or in a helical configuration.

A fluid warming device constructed in accordance with another embodiment of the invention comprises a fluid-carrying tube, a heating component, a temperature sensor, and a control unit. The fluid-carrying tube carries any fluid and broadly comprises a cylindrical outer wall forming an open-ended central channel. The outer wall encloses at least a portion of the heating component and the temperature sensor and includes an opening for allowing the heating component to pass into the outer wall. The opening may be positioned near an end of the fluid-carrying tube so that the heating component may be connected to the control unit near the end of the fluid-carrying tube. The fluid-carrying tube may be formed of rigid or flexible plastic or any other suitable material.

The heating component warms fluid passing through the fluid-carrying tube and broadly comprises a heating element and a connector. The heating element may be a metal wire, etched foil heater, filament, ceramic strip, or any other suitable element at least partially embedded in the outer wall of the fluid-carrying tube. The connector communicatively connects the heating element to the control unit and extends outwardly from the opening of the fluid-carrying tube. The connector may be a USB connector, mini USB connector, 4-pin or 16-pin connector, or any other suitable data connector.

The temperature sensor senses a temperature of the fluid-carrying tube, fluid, or heating element and may be a thermistor, a thermocouple, a silicon bandgap temperature sensor, or any other temperature gauge. The temperature sensor may be embedded in the outer wall of the fluid-carrying tube along with the heating element for obtaining a more accurate temperature reading. Alternatively, the temperature sensor may be integrated with the control unit such that the temperature is obtained as a function of a voltage drop across the heating element, a current draw across the heating element, or any other suitable electronic property.

The control unit includes a controller, a port, a display, a number of user inputs, and a power source. The control unit is substantially similar to the control units described above and is therefore not described in detail here. The control unit may also include a housing configured to retain the controller, port, display, user inputs, and/or power source.

In another embodiment, the outer wall of the fluid-carrying tube comprises an inner layer and an outer layer with the heating element being positioned between the inner layer and outer layer. The heating element may extend beyond proximal ends of the inner layer and outer layer such that the outer wall does not need an opening for the heating element. This simplifies manufacturing of the fluid-carrying tube.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein:

FIG. 3 is an enlarged perspective view of a heating component of the fluid warming device attached to a fluid-carrying tube;

FIG. 4 is an enlarged partial cut-away perspective view of the heating component of FIG. 3;

Figure 1:
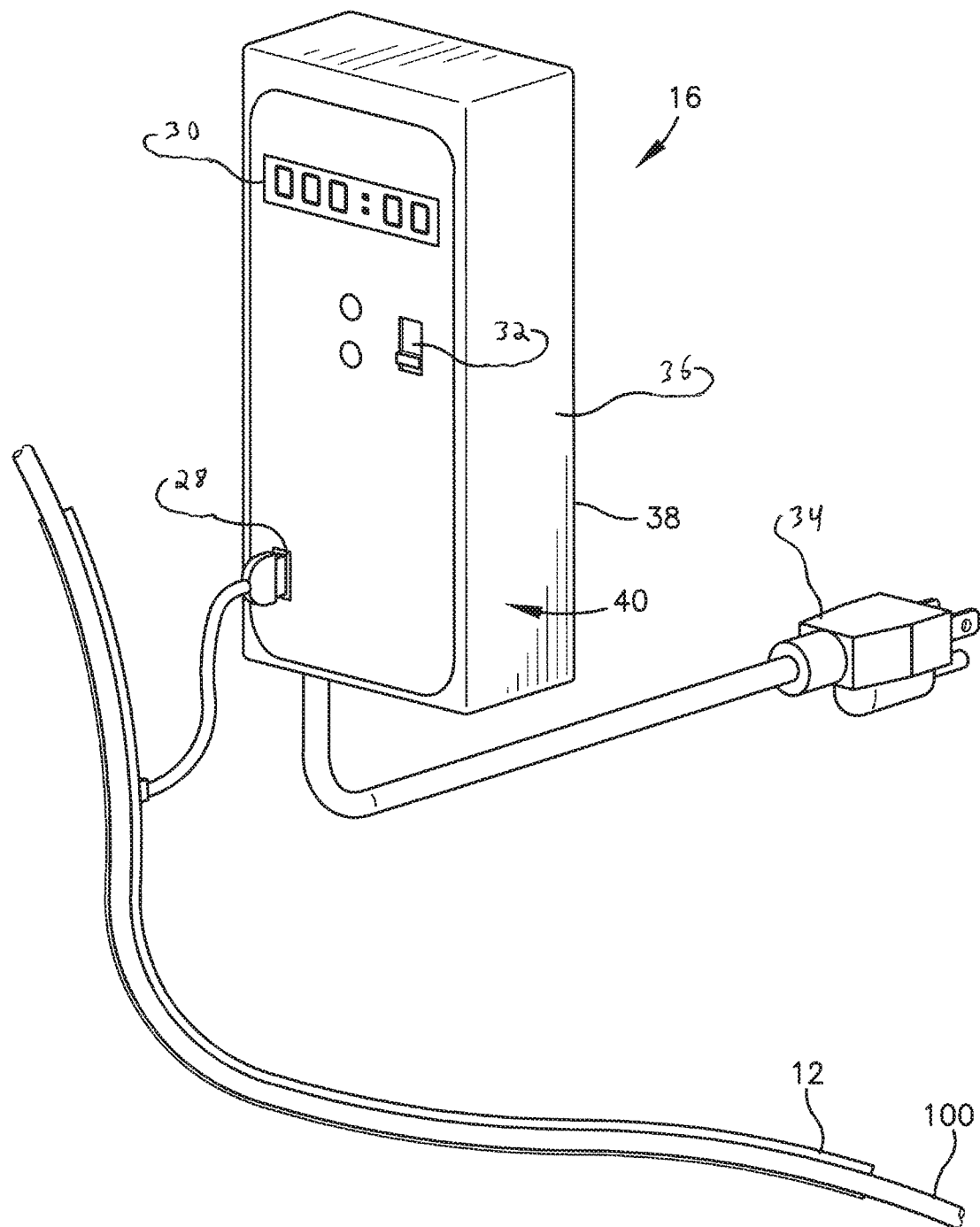
FIG. 1 is a perspective view of a fluid warming device constructed in accordance with an embodiment of the invention.
Figure 2:
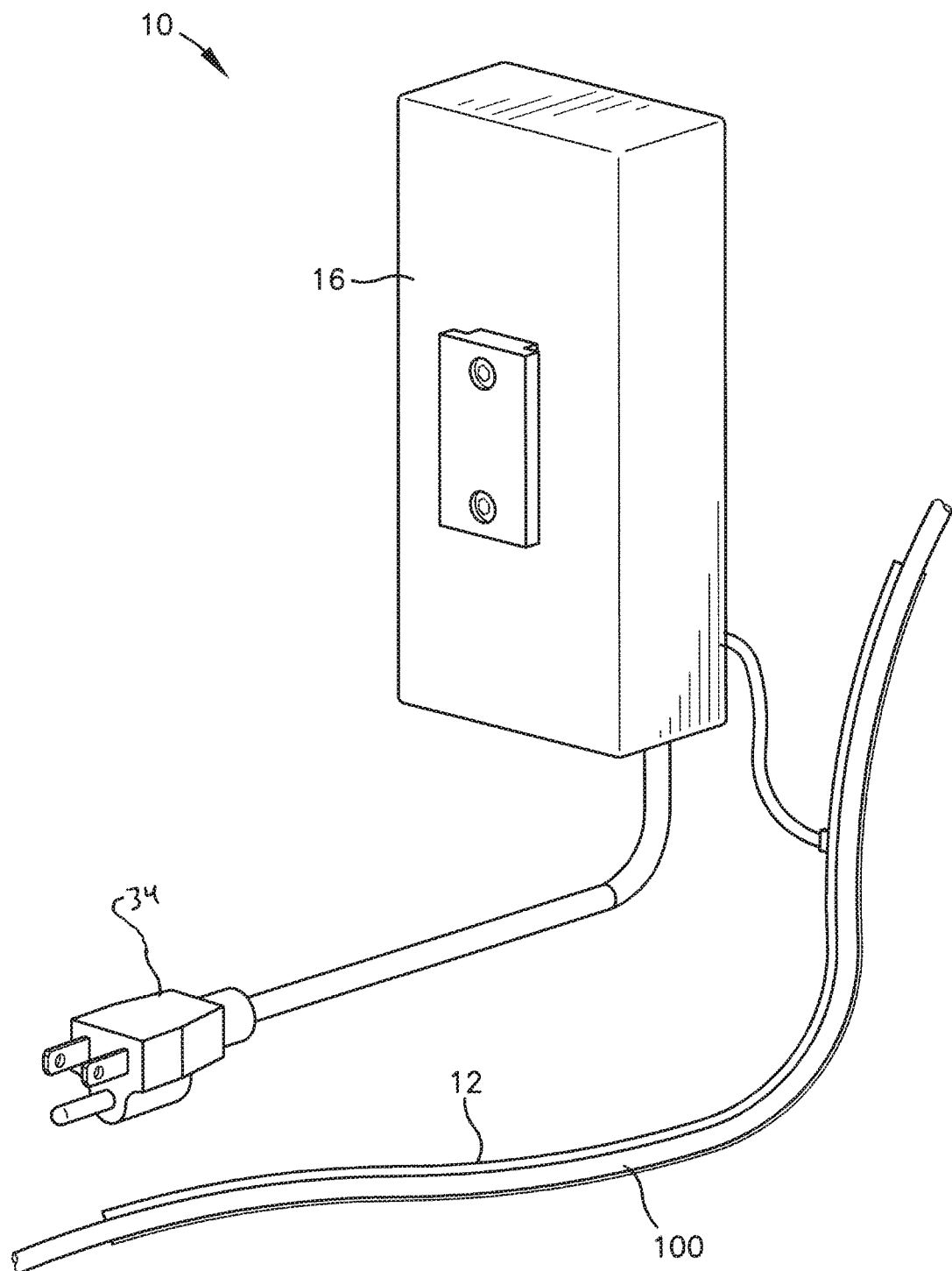
FIG. 2 is a rear perspective view of the fluid warming device of FIG. 1.

The drawing figures do not limit the invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning now to FIGS. 1-7, a fluid warming device 10 constructed in accordance with an embodiment of the invention is illustrated. The fluid warming device 10 is especially configured for use with a fluid-carrying tube 100 or any other medical component that requires heating. For example, the fluid-carrying tube 100 may be an intravenous (IV) tube, an enteral feeding tube, a connector tube, or a syringe. The fluid-carrying tube 100 broadly comprises an outer wall 102 forming an open-ended channel 104 for carrying a fluid from a pump or elevated reservoir, through the channel 104, and into a patient's vein, stomach, or intestine. The fluid-carrying tube 100 may be rigid or flexible plastic or any other suitable material.

The fluid warming device 10 will now be described in detail. The fluid warming device 10 broadly comprises an elongated electrical heating component 12, a temperature sensor 14, and a control unit 16.

Figure 5:
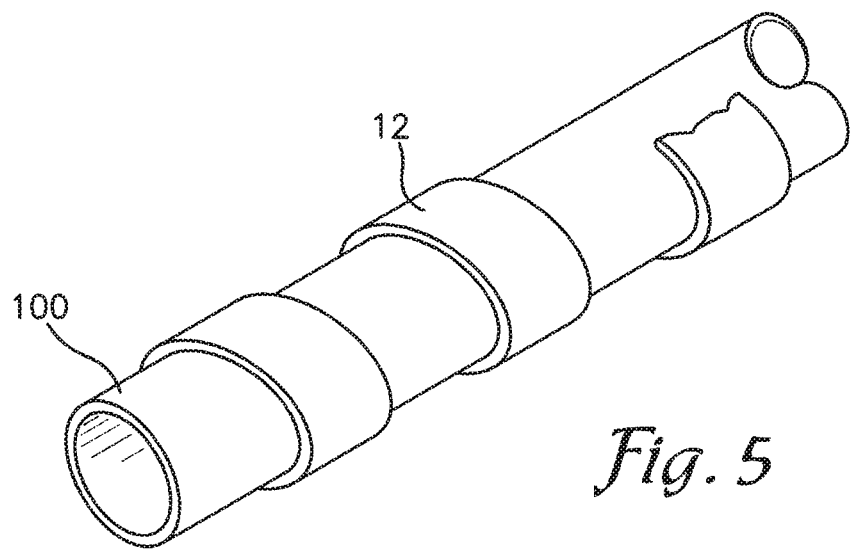
FIG. 5 is a perspective view of the heating component of FIG. 3 wrapped around the fluid-carrying tube in a helical configuration.
Figure 6:
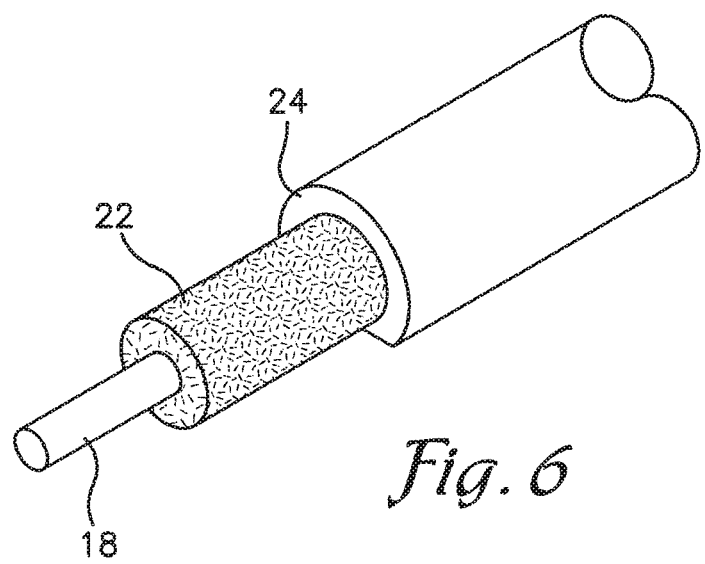
FIG. 6 is an enlarged partial cut-away perspective view of a cylindrical heating component.
Figure 7:
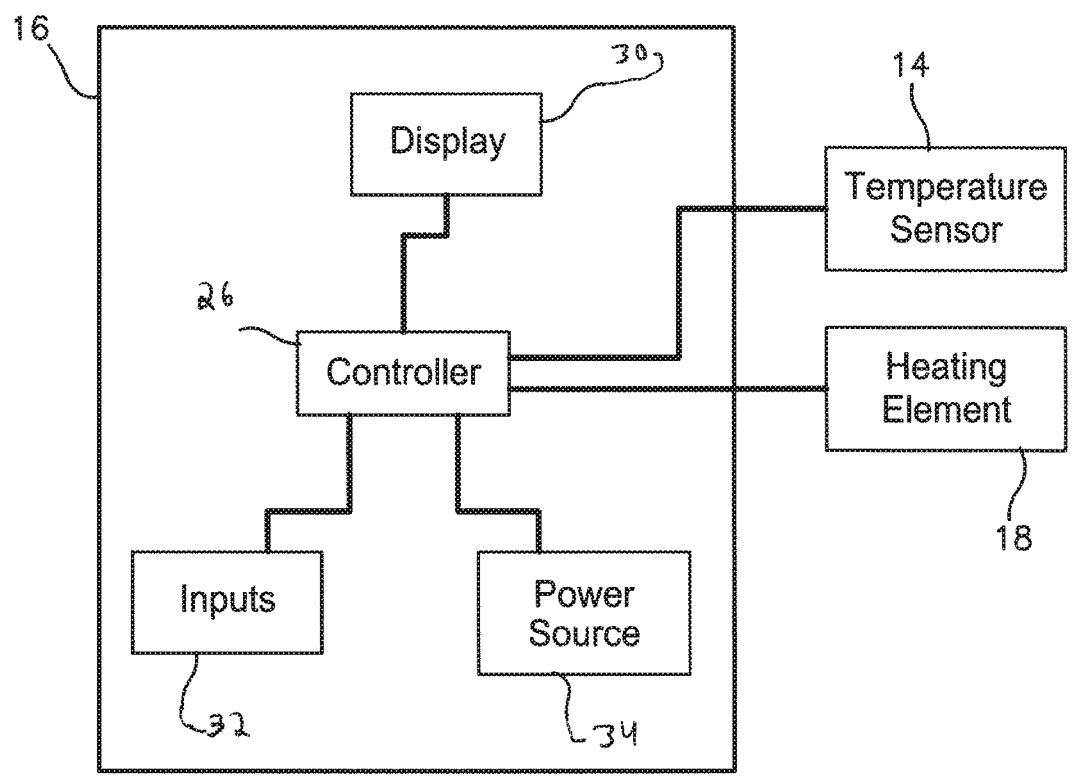
FIG. 7 is a schematic view of the electrical components of the fluid warming device.
Figure 8:
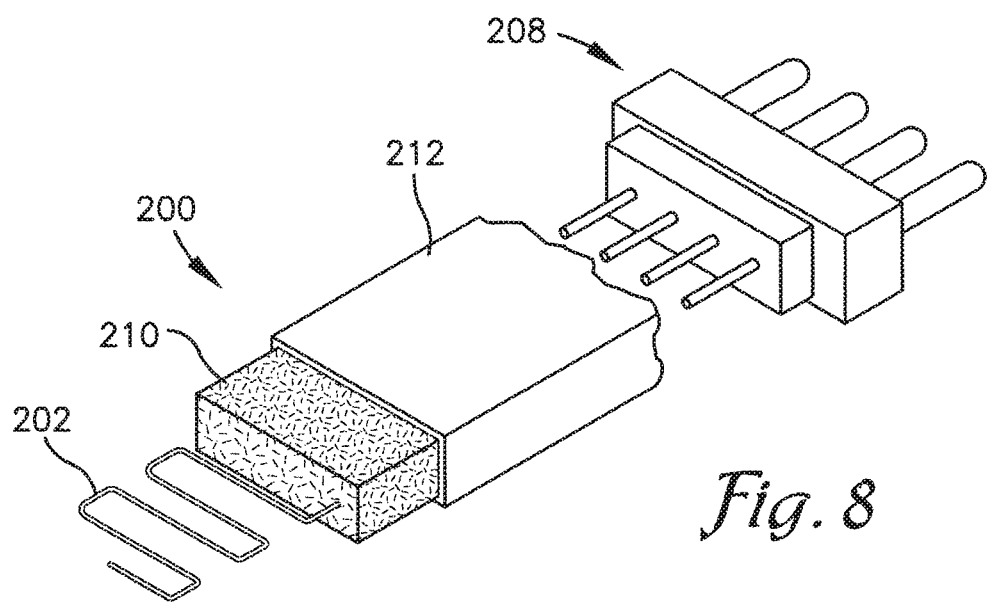
FIG. 8 is an enlarged perspective view of a heating strip constructed in accordance with another embodiment of the invention.
Figure 9:
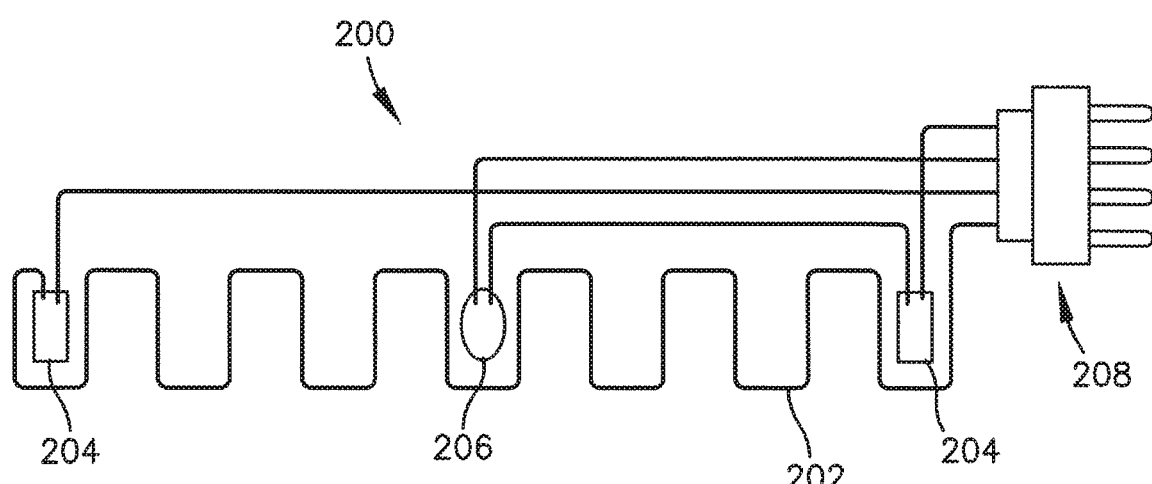
FIG. 9 is an enlarged plan view of the heating element, temperature sensors, overheat sensor, and connector of the heating strip of FIG. 8.
Figure 10:
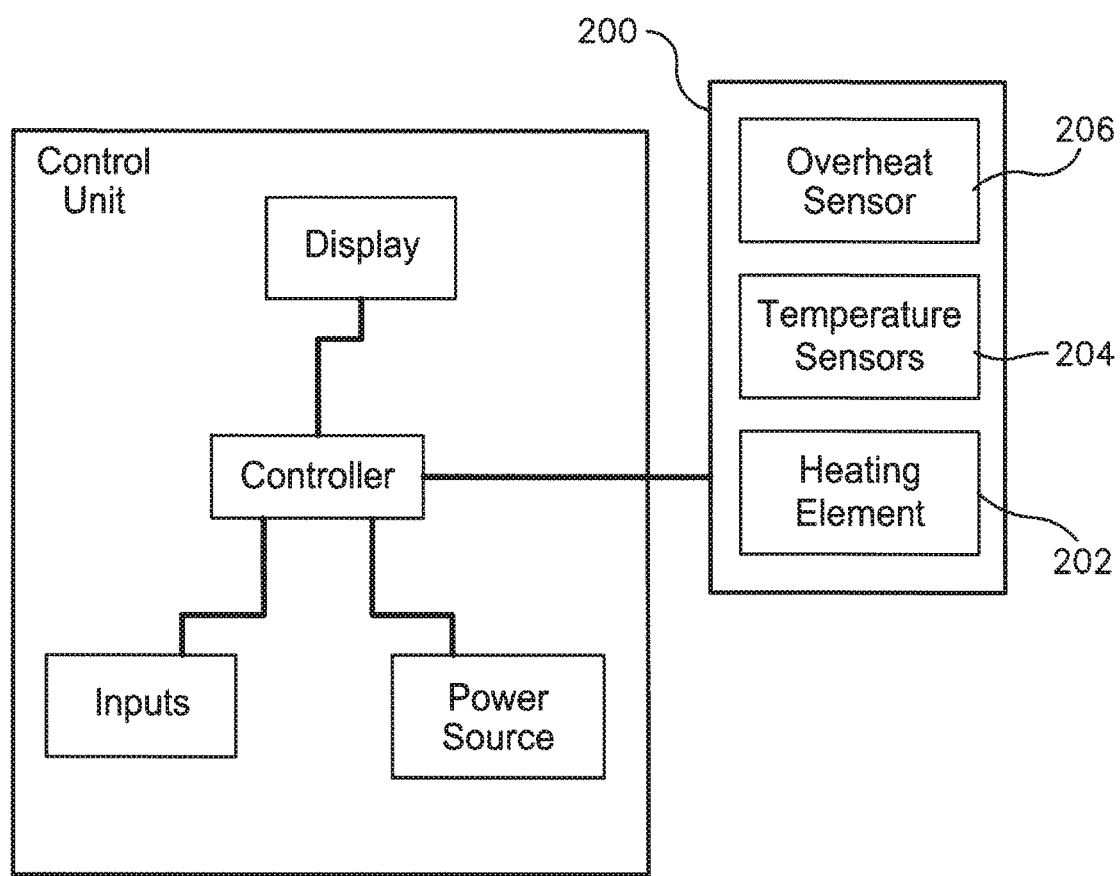
FIG. 10 is a schematic view of the electronic components of FIG. 9.

The electrical heating component 12 warms fluid passing through the fluid-carrying tube 100 and may be a ribbon (FIGS. 3-5) or a cylindrical cable (FIG. 6). The electrical heating component 12 comprises a heating element 18 and a connector 20. The heating element 18 may be a metal wire (e.g., a Nichrome wire), filament, ceramic strip, etched foil heater, or any other suitable heating mechanism that produces resistive heat when subjected to an electrical current. The heating element 18 may also include a heat conductive layer 22 such as teflon, kapton, or silicone and an insulating sheath 24. The layer 22 protects the electrical heating component 12 and may have a high thermal conductivity for allowing heat to pass from the heating element 18 to the fluid-carrying tube 100. The layer 22 may also be flexible, fireproof, and/or waterproof. The insulating sheath 24 at least partially encloses the layer 22 and may have a low thermal conductivity for preventing heat from emanating away from the fluid-carrying tube 100. The insulating sheath 24 may also be flexible, fireproof, and/or waterproof. The electrical heating component 12 may be at least partially coated with an adhesive for temporarily or permanently attaching the electrical heating component 12 to the fluid-carrying tube 100. Alternatively, at least a portion of the electrical heating component 12, such as the heating element 18, may be embedded in the fluid-carrying tube 100.

The connector 20 communicatively connects the electrical heating component 12 to the control unit 16 and may be a USB connector, mini USB connector, 4-pin or 16-pin connector, or any other suitable data connector. The connector 20 may include separate electrical contacts for the heating element 18 and temperature sensor 14. Alternatively, separate connectors may be used for powering the heating element 18, delivering data from the temperature sensor 14 to the control unit 16, and controlling other components. As another alternative, the electrical heating component 12 may be configured to communicate with the control unit 16 wirelessly such as via radio frequency signal transmissions, near frequency communication (NFC) technology, or the like.

The temperature sensor 14 senses a temperature of the fluid-carrying tube 100, the fluid, or the heating element 18 and may be a thermistor, a thermocouple, a silicon bandgap temperature sensor, or any other temperature gauge. The temperature sensor 14 may be positioned near or integrated with the electrical heating component 12 for obtaining a more accurate temperature reading. The temperature sensor 14 may also be embedded in the fluid-carrying tube 100. The temperature sensor 14 may communicate with the control unit 16 via the connector 20 of the electrical heating component 12 or wirelessly via radio frequency signal transmissions, near frequency communication (NFC) technology, or the like. Alternatively, the temperature sensor 14 may be integrated with the control unit 16 such that the temperature is obtained as a function of a voltage drop across the heating element 18, a current draw across the heating element 18, or any other suitable electronic property. As another alternative, the temperature sensor 14 may be configured to sense a temperature of the heating element 18. For example, the temperature sensor 14 may be positioned near an end of the heating element 18, with another temperature sensor being positioned near an opposite end of the heating element 18 such that a temperature difference between the two opposing temperature sensors may be used to determine a heating level of the heating element 18. Additional temperature sensors, and different types of temperature sensors may be used for more accurate temperate readings and more complete data collection.

The control unit 16 controls and powers the electrical heating component 12 in response to temperatures sensed by the temperature sensor 14 and broadly comprises a controller 26, a port 28, a display 30, one or more user inputs 32, and a power source 34. The control unit 16 may be a computer, laptop, tablet, mobile device, handheld remote, or any other suitable computing device.

The controller 26 regulates a heating level of the heating element 18 and controls the display 24. The controller 26 may include a printed circuit board (PCB), a memory, and/or other electronic components and may be connected to the heating element 18 and the temperature sensor 14 via the port 28.

The controller 26 may implement aspects of the invention with one or more computer programs stored in or on computer-readable medium residing on or accessible by the controller 26. Each computer program preferably comprises an ordered listing of executable instructions for implementing logical functions in the controller 26. Each computer program can be embodied in any non-transitory computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can store the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The port 28 receives the connector 20 of the electrical heating component 12 for communicatively connecting the heating component 12 and/or temperature sensor 14 to the controller 26. The port 28 may be a USB port, mini USB port, 4-pin or 16-pin port, or any other suitable data port. Alternatively, a number of ports may be used to connect the heating component 12, temperature sensor 14, and other components to the controller 26. As yet another alternative, the controller 26 may be configured to communicate with the heating component 12 wirelessly such as via radio frequency signal transmissions, near frequency communication (NFC) technology, or the like via a transceiver or other suitable wireless communication component.

The display 30 provides a visual indication of the temperature of the fluid-carrying tube 100 and other information and may be a seven segment LCD display, an analog display, a touch screen, or any other display. The display 30 may include additional LED lights and other indicators for providing additional information to the user.

The user inputs 32 allow the user to turn the warming device 10 on and off, to program the warming device 10, to reset the warming device 10, and to perform other functions and may include switches, buttons, dials, and other user inputs. The user inputs 32 may comprise a power button or power switch, a reset button, a calibration button, a temperature unit toggle button, and other inputs. The power source 34 supplies electrical power to the electrical heating component 12, temperature sensor 14, controller 26, and display 20 and includes a power cord for connecting to a 100 volt or 240 volt, 60 W/hr or 100 W/hr, 50/60 Hz outlet, or any other power outlet.

In some embodiments, the control unit 16 may also comprise a housing 36 including an outer wall 38 forming an internal chamber 40 for enclosing and protecting the components of the warming device 10. The outer wall 38 may also include a port opening 42 for providing access to the port 28. The controller 26 may be positioned in the internal chamber 40 and the display 30 may be mounted in a front opening of the housing 36 facing outward from the housing 12 and connected to the controller 26. The housing 36 may be approximately 7 inches long, 3.25 inches wide, and 2 inches deep and may be formed of water resistant plastic or any other suitable material.

Operation of the fluid warming device 10 will now be described in more detail. First, the fluid-carrying tube 100 may be connected to a fluid supply via a pump. The fluid may also be gravity fed. The electrical heating component 12 may then be attached to or positioned near the fluid-carrying tube 100. For example, the electrical heating component 12 may be attached longitudinally to the fluid-carrying tube 100 via an adhesive. Alternatively, the electrical heating component 12 may be wrapped in a helical configuration around the fluid-carrying tube 100, as shown in FIG. 5. Increasing an effective longitudinal engagement length between the electrical heating component 12 and the fluid-carrying tube 100 and wrapping the electrical heating component 12 around the fluid-carrying tube 100 improve heat transfer between the electrical heating component 12 and the fluid-carrying tube 100.

The temperature sensor 14 may be positioned near a downstream end of the fluid-carrying tube 100 such that temperature readings obtained by the temperature sensor 14 more closely represent a temperature of the fluid after the fluid passes through the warmed portion of the fluid-carrying tube 100. As mentioned above, the temperature sensor 14 may instead be integrated with the electrical heating component 12 or the controller 26.

The fluid warming device 10 may then be turned on by plugging in the power source 34 or pressing the power button of the user inputs 32. The controller 20 will initiate a power on sequence in which it instructs the display 30 to display an indication that the fluid warming device 10 is fully operational. If the controller 20 or other components of the fluid warming device 10 are not fully operational, the controller 20 may generate an error message and instruct the display 30 to display the error message indicating to the user that the fluid warming device 10 or a component of the fluid warming device 10 should be serviced. The controller 20 will activate the electrical heating component 12 if the fluid warming device 10 is fully functional so that the electrical heating component 12 begins to warm the fluid-carrying tube 100.

The controller 26 monitors the temperature of the fluid-carrying tube 100 by sending a signal to the temperature sensor 14, which returns a signal representative of the temperature to the controller 26. The controller 26 instructs the display 30 to display the temperature of the fluid-carrying tube 100. If the temperature is less than a predetermined threshold temperature, such as 90° F. (32° C.), the heating element 18 continues to warm the fluid-carrying tube 100 and the controller 26 instructs the display 30 to indicate via an LED light that the fluid warming device 100 is not ready to warm the fluid. Warming the fluid-carrying tube 100 from room temperature to the predetermined lower threshold temperature should take approximately 2 to 3 minutes.

The controller 26 instructs the display 30 to indicate via another LED light that the fluid warming device 10 is ready to warm the fluid when the fluid-carrying tube 100 reaches the predetermined lower threshold temperature. A second end of the fluid-carrying tube 100 may then be inserted into the patient's stomach, intestine, or vein and the pump may then be activated. The pump draws the fluid from the fluid supply and may force it through the fluid-carrying tube 100 at a flow rate of approximately 0.25 ml/min to approximately 1 ml/min. The fluid may also be gravity fed. The warm fluid-carrying tube 100 warms the fluid to a temperature within the TNZ as it passes through the fluid-carrying tube 100. The warmed fluid is then delivered into the patient's stomach, intestine, or vein via the second end of the fluid-carrying tube 100.

At any time during operation, the controller 26 will temporarily deactivate the electrical heating component 12 if the temperature of the fluid-carrying tube 100 is greater than a predetermined upper threshold temperature, such as 103° F. (39° C.). The controller 26 will reactivate the electrical heating component 12 when the temperature of the fluid-carrying tube 100 drops to the predetermined lower threshold temperature or when the temperature of the fluid-carrying tube 100 drops to an intermediate temperature as described below. This ensures that the temperature of the fluid exiting the fluid-carrying tube 100 is within the TNZ.

The controller 26 may maintain the temperature of the fluid-carrying tube 100 at an intermediate temperature, such as 95° F. (35° C.), or within an intermediate temperature range, such as 93° F. (34° C.) to 97° F. (36° C.), by frequently activating and deactivating the electrical heating component 12 when the temperature of the fluid-carrying tube 100 reaches these temperatures. This allows the temperature of the fluid-carrying tube 100, and hence the temperature of the fluid being delivered into the patient's vein, stomach, or intestine to remain relatively constant during operation instead of rising and falling between the upper and lower threshold temperatures of the TNZ.

It will be understood that one or more of the above-described steps may be performed in a different order than described or simultaneously. For example, the fluid warming device 10 may be turned on before the fluid-carrying tube 100 is connected to the output of the pump. As another example, the controller 26 may activate the electrical heating component 12 before the electrical heating component 12 is attached to the fluid-carrying tube 100.

The above-described fluid warming device 10 provides several advantages over conventional devices. For example, the fluid warming device 10 gradually warms fluid to a temperature in the TNZ. The elongated electrical heating component 12 increases exposure of the fluid to the heat generated by the heating element 18 for an extended duration of time. The extended exposure allows the warming device 10 to warm the fluid to a temperature within the TNZ without using high heat to warm the fluid. This prevents the nutrients in the fluid from breaking down and prevents the fluid-carrying tube 100 from introducing foreign particles into the fluid. Importantly, the electrical heating component 12 is configured to be connected to the control unit 16 via the port 28, which allows the electrical heating component 12 to be attached to or positioned near the fluid-carrying tube 100 without the control unit 16 being positioned near the fluid-carrying tube 100.

Turning now to FIGS. 8-11, a fluid warming device constructed in accordance with another embodiment of the invention is illustrated. The fluid warming device broadly comprises a heating strip 200 and a control unit.

Figure 11:
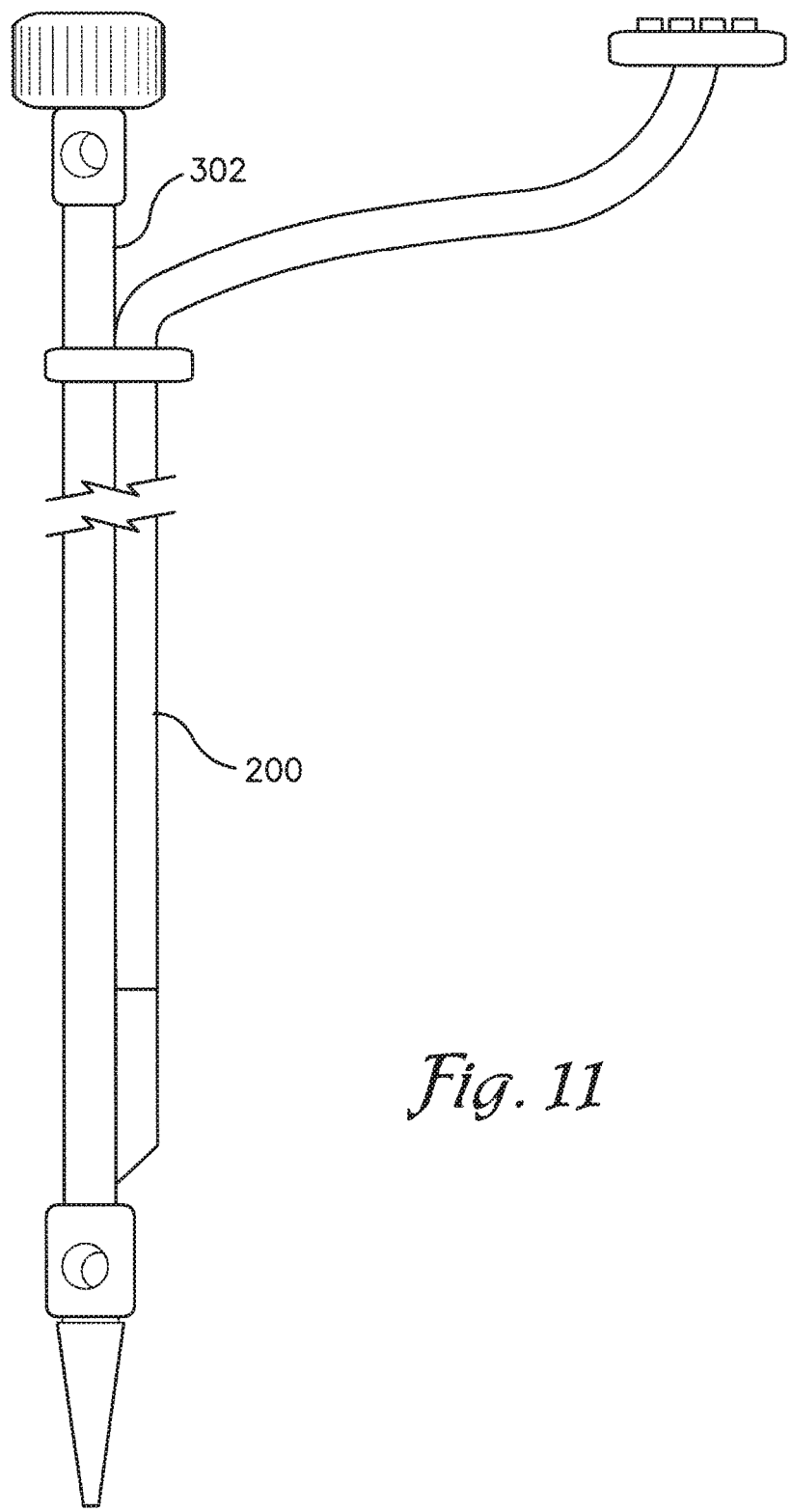
FIG. 11 is a perspective view of the heating strip of FIG. 8 attached to a catheter connector.

The heating strip 200 combines heating and temperature sensing functions and broadly comprises an electrical heating element 202, one or more temperature sensors 204, an overheat sensor 206, and a connector 208. The heating strip 200 may be a flat tape or flat ribbon, a round cable, or other suitable elongated strip configured to be attached to or positioned near a fluid-carrying tube 300. The heating strip 200 may also be used with a connector 302 or other similar fluid delivery component, as shown in FIG. 11.

The electrical heating element 202 warms fluid passing through the fluid-carrying tube 300 or other fluid delivery component and may be an etched foil heater, a metal wire (e.g., a Nichrome wire), filament, ceramic strip, or any other suitable mechanism that produces resistive heat when subjected to an electrical current. The heating element 202 may extend from a first end of the heating strip 200 to a second end of the heating strip 200 and back towards the first end so as to form a loop. The heating element 202 may also extend laterally back and forth along the heating strip 200 to increase an overall heat output along the fluid-carrying tube 300. The heating element 202 may also include a heat conductive layer 210 and insulating sheath 212. The heat conductive layer 210 protects the heating element 202 and may have a high thermal conductivity for allowing heat to pass from the heating element 202 to the fluid-carrying tube 300. The layer 210 may also be flexible, fireproof, and/or waterproof. The insulating sheath 212 at least partially encloses the layer 210 and may have a low thermal conductivity for preventing heat from emanating away from the fluid-carrying tube 100. The insulating sheath 212 may also be flexible, fireproof, and/or waterproof.

The temperature sensors 204 sense a temperature of the fluid-carrying tube 300 and may be thermistors, thermocouples, silicon bandgap temperature sensors, or any other temperature gauges. One temperature sensor 204 may be positioned near a proximal end of the heating element 202 while a second temperature sensor 204 may be positioned near a distal end of the heating element 202 for obtaining more complete temperature readings.

The overheat sensor 206 senses an overheating condition for preventing the heating element 202 from warming the fluid-carrying tube 300 to a temperature above an upper limit of the TNZ or another predetermined temperature. The overheat sensor 206 may also prevent the heating element 202 from damaging the heat conductive layer 210 and/or the insulating sheath 212. The overheat sensor 206 may be positioned near a midpoint of the heating element 202 so as to ensure that overheating is detected as early as possible.

The overheat sensor may comprise a single sensor that shuts off or turns down the heating element once the tube reaches a particular temperature or it may comprise several sensors that form a redundant multi-stage sensor assembly that that shuts off or turns down the heating element at several successive temperatures. The multi-stage sensor assembly provides redundant temperature protection in case any of the sensors fail.

The connector 208 communicatively connects the heating element 202, temperature sensors 204, and overheat sensor 206 to the control unit. The connector 208 may be a USB connector, mini USB connector, 4-pin or 16-pin connector, or any other suitable data connector. The connector 208 may include separate electrical contacts for the heating element 202, temperature sensor 204, and overheat sensor 206.

The control unit broadly comprises a controller, a port, a display, user inputs, and a power source substantially similar to the components described above and thus these components will not be described here. In some embodiments, the control unit may further comprise a housing similar to the housing described above for retaining the controller, port, display, user inputs, and/or power source.

Operation of the fluid warming device will now be described in more detail. First, the fluid-carrying tube 300 may be connected to a fluid supply via a pump. Or, the fluid may be gravity fed. The heating strip 200 may then be attached to or positioned near the fluid-carrying tube 300. For example, the heating strip 200 may be attached longitudinally to the fluid-carrying tube 100 via an adhesive. Alternatively, the heating strip 200 may be wrapped in a helical configuration around the fluid-carrying tube 300. Increasing an effective longitudinal engagement length between the heating strip 200 and the fluid-carrying tube 300 and wrapping the heating strip 200 around the fluid-carrying tube 300 improve heat transfer between the heating strip 200 and the fluid-carrying tube 300. The connector 208 of the heating strip 200 may then be connected to the port such that the heating element 202, temperature sensors 204, and overheat sensor 206 are communicatively coupled to the controller.

The fluid warming device may then warm the fluid-carrying tube 300 as described above. The temperature sensors 204 each may generate a signal representative of a temperature of the fluid-carrying tube 300. The downstream temperature sensor 204 will provide a higher temperature reading than the upstream temperature sensor 204. The controller may use this difference to determine a rate of temperature increase, a heat transfer efficiency, or other information.

At any time, the overheat sensor 206 may generate a signal representative of an overheating condition. The overheating condition may be a temperature near or at an upper level of the TNZ or another predetermined maximum allowed fluid temperature. The overheating condition may also be a maximum allowed temperature of the temperature sensors 204, ceramic felt layer 210, or insulating sheath 212. The controller will then turn off or decrease a heat level of the heating element 202. The controller may also instruct the display to indicate that an overheating condition has occurred or that the fluid warming device needs to be serviced. The controller may then turn on or increase the heat level of the heating element 202 if the overheat sensor 206 no longer senses an overheat condition.

The above-described fluid warming device provides several advantages over conventional devices. For example, the heating strip 200 combines heating and temperature sensing functions into a single component. The heating element 202 may extend laterally back and forth along the heating strip 200, which increases heat output along the heating strip 200. The plurality of temperature sensors 204 allows for more accurate and more complete temperature and heat transfer monitoring. The overheat sensor 206 prevents the heating element 202 from warming the fluid and/or fluid-carrying tube 300 to temperatures above predetermined thresholds. The overheat sensor 206 may also prevent the heating element 202 from causing heat damage to components in the heating strip 200. Importantly, the heating strip 200 is configured to be connected to the controller via the port 28 or a wireless connection, which allows the heating strip 200 to be attached to or positioned near the fluid-carrying tube 300 without the control unit being positioned near the fluid-carrying tube 300. The heating strip 200 is also configured to be attached to the fluid-carrying tube 300 longitudinally or in a helical configuration.

Figure 12:
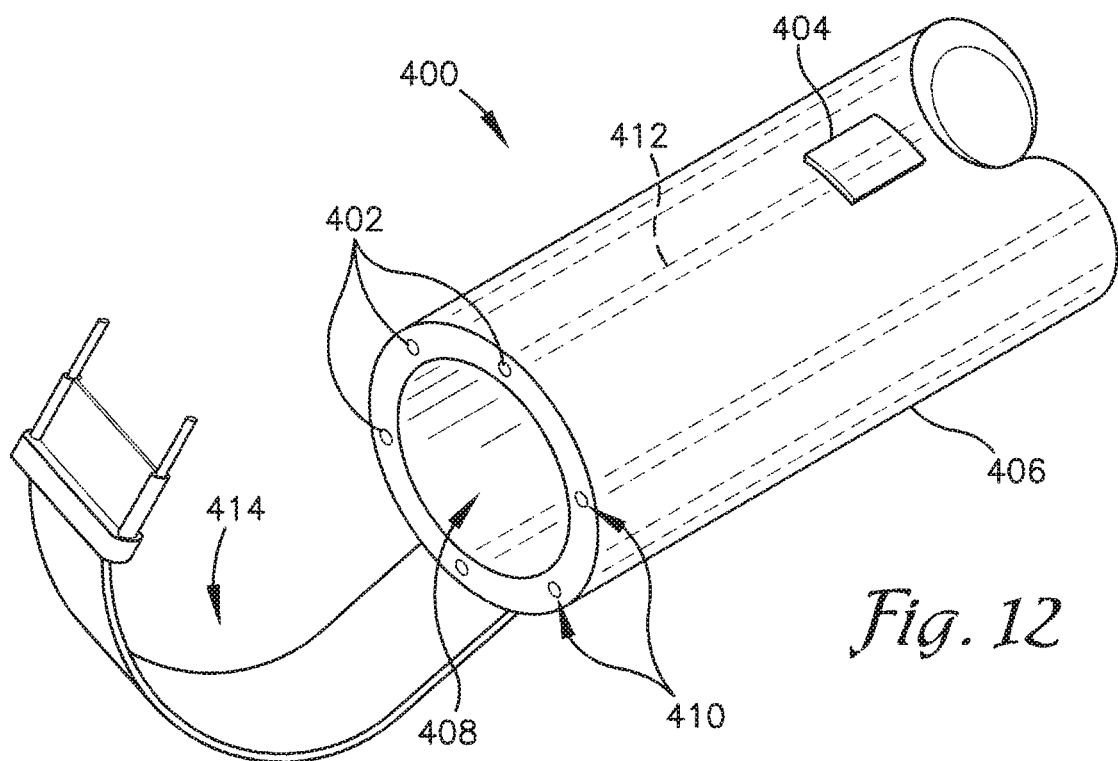
FIG. 12 is an enlarged partial cut-away perspective view of a fluid-carrying tube and heating element constructed in accordance with another embodiment of the invention.

Turning to FIG. 12, a fluid warming device constructed in accordance with another embodiment of the invention is illustrated. The fluid warming device broadly comprises a fluid-carrying tube 400, an electrical heating component 402, a temperature sensor 404, and a control unit.

The fluid-carrying tube 400 carries intravenous fluid, enteral feeding fluid, or any other fluid and broadly comprises a cylindrical outer wall 406 forming an open-ended central channel 408. The outer wall 406 encloses the electrical heating component 402 and the temperature sensor 404 and includes an opening 410 for allowing the electrical heating component 402 to pass through the outer wall 406. The opening 410 may be positioned near an end of the fluid-carrying tube 400 so that the electrical heating component 402 may be connected to the control unit near the end of the fluid-carrying tube 400. The fluid-carrying tube 400 may be formed of rigid or flexible plastic or any other suitable material.

The electrical heating component 402 warms fluid passing through the fluid-carrying tube 400 and broadly comprises an electrical heating element 412 and a connector 414. The heating element 412 may be a metal wire, an etched foil heater, filament, ceramic strip, or other heating mechanism at least partially embedded in the outer wall 406 of the fluid-carrying tube 400. The connector 414 is configured to connect the heating element 412 to the control unit through the opening 410 of the fluid-carrying tube 400 and may be a USB connector, mini USB connector, 4-pin or 16-pin connector, or any other suitable data connector.

The temperature sensor 404 senses a temperature of the fluid-carrying tube 400 and may be a thermistor, a thermocouple, a silicon bandgap temperature sensor, or any other temperature gauge. The temperature sensor 404 may be embedded in the outer wall 406 of the fluid-carrying tube 400 along with the electrical heating component 402 for obtaining a more accurate temperature reading. Alternatively, the temperature sensor 404 may be integrated with the control unit such that the temperature is obtained as a function of a voltage drop across the heating element 412, a current draw across the heating element 412, or any other suitable electronic property. An overheat sensor, similar to the overheat sensor described above, may also be embedded in the outer wall 406 along with the temperature sensor 404 for ensuring that the temperature of the fluid-carrying tube 400 exceeds an upper limit of the TNZ or other predetermined upper limit.

The control unit broadly comprises a controller, a port, a display, user inputs, and a power source substantially similar to the components described above and thus these components will not be described here. In some embodiments, the control unit may also comprise a housing similar to the housings described above for retaining the controller, port, display, user inputs, and/or power source.

The above-described fluid-warming device provides several advantages over conventional devices. For example, the heating element 412 is at least partially embedded in the outer wall 406 of the fluid-carrying tube 400, which improves heat transfer between the heating element 412 and the fluid-carrying tube 400. This also reduces the overall number of components, thus simplifying assembly and operation of the fluid warming device. The heating element 412 is also protected from wear and tear in the outer wall 406 of the fluid-carrying tube 400.

Figure 13:
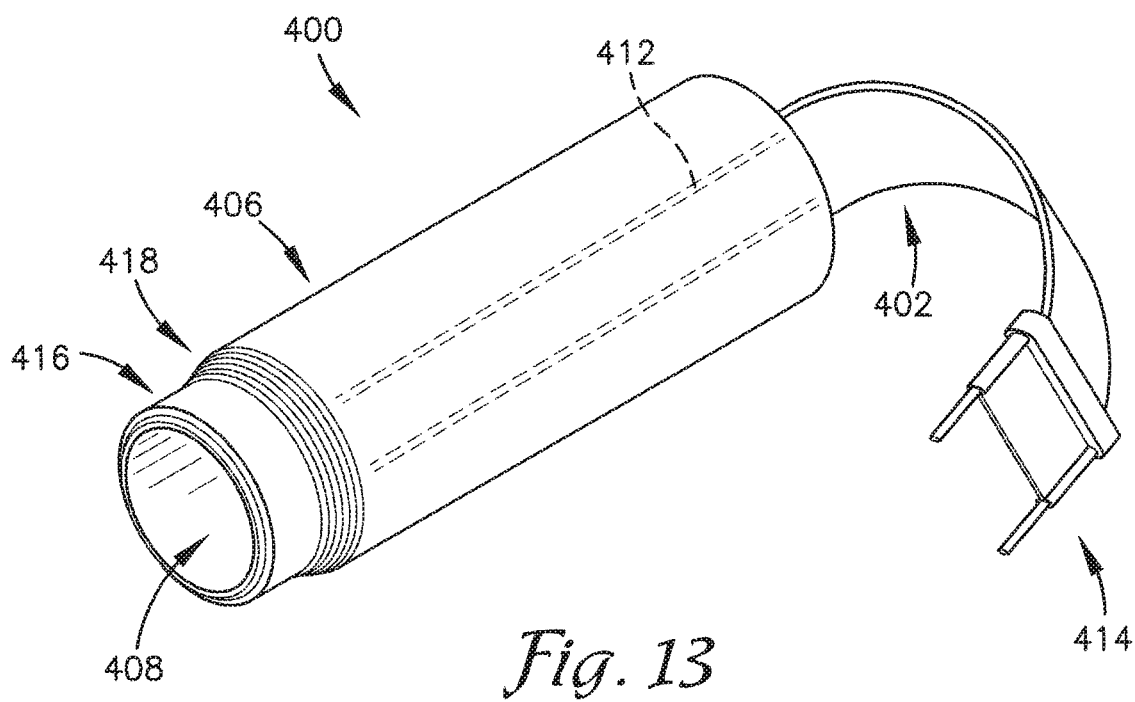
FIG. 13 is an enlarged partial cut-away perspective view of a fluid-carrying tube and heating element constructed in accordance with another embodiment of the invention.

In another embodiment, the outer wall 406 of the fluid-carrying tube 400 comprises an inner layer 416 and an outer layer 418, as shown in FIG. 13. The heating element 412 is positioned between the inner layer 416 and outer layer 418, which simplifies manufacturing of the fluid-carrying tube 400.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A fluid warming device comprising:
    an elongated heating strip configured to be attached to a fluid-carrying tube, the heating strip comprising:
        a heating element configured to heat the fluid-carrying tube for warming fluid passing through the fluid-carrying tube, the heating element having opposing first and second ends;
        a first temperature sensor for sensing a temperature of the fluid-carrying tube or fluid within the fluid-carrying tube near the first end of the heating element;
        a second temperature sensor for sensing a temperature of the fluid-carrying tube or fluid within the fluid-carrying tube near the second end of the heating element;
        an overheat sensor positioned between the first temperature sensor and the second temperature sensor for sensing an overheat condition;
        a connector coupled to the heating element;
        adhesive for attaching the heating strip to the fluid-carrying tube;
        a heat conductive layer at least partially enclosing the heating element; and
        an insulating sheath at least partially enclosing the heat conductive layer; and
    a control unit comprising:
        a port into which the connector of the heating strip may be plugged, the port being configured to provide electrical power to the heating element and receive signals from the temperature sensor; and
        a controller coupled with the port for controlling a heating level of the heating element in response to the temperature sensed by the temperature sensor, the controller being configured to turn off or lower a heating level of the heating element in response to the overheat sensor sensing the overheat condition.

2. The fluid warming device of claim 1, wherein the heating strip is configured to be wrapped around the fluid-carrying tube in a helical configuration.

3. The fluid warming device of claim 1, wherein the connector includes separate electrical contacts for the heating element, first temperature sensor, second temperature sensor, and overheat sensor.

4. A fluid warming device comprising:
 a heating strip configured to be attached to a catheter connector, the heating strip comprising:
  a heating element configured to heat the catheter connector for warming fluid passing through the catheter connector, the heating element having opposing first and second ends;
  a first temperature sensor for sensing a temperature of the catheter connector or fluid within the catheter connector near the first end of the heating element;
  a second temperature sensor for sensing a temperature of the catheter connector or fluid within the catheter connector near the second end of the heating element;
  an overheat sensor positioned between the first temperature sensor and the second temperature sensor for sensing an overheat condition;
  a connector coupled to the heating element;
  an adhesive for attaching the heating strip to the catheter connector;
  a heat conductive layer at least partially enclosing the heating element; and
  an insulating sheath at least partially enclosing the heat conductive layer; and
 a control unit comprising:
  a port into which the connector of the heating strip may be plugged, the port being configured to provide electrical power to the heating element and receive signals from the temperature sensor; and
  a controller coupled with the port for controlling a heating level of the heating element in response to the temperature sensed by the temperature sensor, the controller being configured to turn off or lower a heating level of the heating element in response to the overheat sensor sensing the overheat condition.

5. A fluid warming device comprising:
 an elongated electrical heating component configured to be attached to a fluid-carrying tube, the electrical heating component comprising a heating element configured to heat the fluid-carrying tube for warming fluid passing through the fluid-carrying tube, the heating element having opposing first and second ends and a midpoint between the opposing first and second ends;
 a first temperature sensor for sensing a temperature of the fluid-carrying tube or fluid within the fluid-carrying tube near the first end of the heating element;
 a second temperature sensor for sensing a temperature of the fluid-carrying tube or fluid within the fluid-carrying tube near the second end of the heating element;
 an overheat sensor positioned between the first temperature sensor and the second temperature sensor near the midpoint of the heating element for sensing an overheat condition;
 an adhesive for attaching the heating strip to the fluid-carrying tube;
 a heat conductive layer at least partially enclosing the heating element; and
 an insulating sheath at least partially enclosing the heat conductive layer; and
 a control unit comprising:
  a transceiver configured to receive a signal representative of the temperature sensed by the temperature sensor and a signal representative of the overheat condition from the overheat sensor and transmit a signal representative of a desired heating level to the heating element; and
  a controller coupled to the transceiver and configured to control the heating element in response to the temperature sensed by the temperature sensor via the transceiver, the controller being configured to turn off or lower a heating level of the heating element if the overheat sensor senses the overheat condition.

* * * * *